(12) United States Patent
Müller et al.

(10) Patent No.: US 8,119,107 B2
(45) Date of Patent: Feb. 21, 2012

(54) PHOTO-STABLE COSMETIC OR DERMATOLOGICAL COMPOSITIONS

(75) Inventors: Stefan Müller, Weil am Rhein (DE); Bernd Herzog, Grenzach-Wyhlen (DE); Katja Quass, Rheinfelden (DE)

(73) Assignee: BASF SE, Ludwigshafen (DE)

( * ) Notice: Subject to any disclaimer, the term of this patent is extended or adjusted under 35 U.S.C. 154(b) by 1084 days.

(21) Appl. No.: 11/663,610

(22) PCT Filed: Sep. 19, 2005

(86) PCT No.: PCT/EP2005/054641
§ 371 (c)(1),
(2), (4) Date: Mar. 22, 2007

(87) PCT Pub. No.: WO2006/034968
PCT Pub. Date: Apr. 6, 2006

(65) Prior Publication Data
US 2010/0143272 A1    Jun. 10, 2010

(30) Foreign Application Priority Data

Sep. 29, 2004  (EP) .................................... 04104739
Dec. 22, 2004  (EP) .................................... 04106828

(51) Int. Cl.
*A61Q 17/02* (2006.01)

(52) U.S. Cl. .......... 424/59; 424/401; 514/685; 558/400

(58) Field of Classification Search ................ 424/401, 424/61, 59; 514/685; 558/400
See application file for complete search history.

(56) References Cited

U.S. PATENT DOCUMENTS

| | | | |
|---|---|---|---|
| 5,306,486 A | 4/1994 | McCook et al. | 424/59 |
| 5,576,354 A * | 11/1996 | Deflandre et al. | 514/685 |
| 6,416,773 B2 | 7/2002 | Heidenfelder et al. | 424/401 |
| 7,204,973 B2 | 4/2007 | Goppel et al. | 424/59 |
| 7,341,712 B2 * | 3/2008 | Goppel et al. | 424/59 |
| 2003/0161793 A1 | 8/2003 | Candau | 424/59 |
| 2004/0166072 A1 | 8/2004 | Bonda | 424/59 |
| 2005/0031556 A1 | 2/2005 | Goppel et al. | 424/59 |
| 2006/0073106 A1 | 4/2006 | Berg-Schultz et al. | 424/59 |

FOREIGN PATENT DOCUMENTS

| | | |
|---|---|---|
| DE | 101 55 865 | 5/2003 |
| DE | 101 57 489 | 6/2003 |
| EP | 1 129 695 | 9/2001 |
| EP | 1 310 236 | 5/2003 |
| EP | 1 310 239 | 5/2003 |
| EP | 1 323 412 | 7/2003 |
| WO | 91/11989 | 8/1991 |
| WO | 99/33439 | 7/1999 |
| WO | 03/039506 | 5/2003 |
| WO | 03/053393 | 7/2003 |
| WO | 2004/069216 | 8/2004 |

OTHER PUBLICATIONS

English language abstract of DE 101 55 865 printed on Jul. 18, 2007 from the esp@cenet web site.
English language abstract of EP 1 310 236 printed on Jul. 18, 2007 from the esp@cenet web site.
English language abstract of EP 1 310 239 printed on Jul. 18, 2007 from the esp@cenet web site.
English language abstract of WO 91/11989 printed on Jul. 19, 2007 from the esp@cenet web site.
English language abstract of DE 101/57 489 printed on Jul. 18, 2007 from the esp@cenet web site.

* cited by examiner

*Primary Examiner* — Gina C Yu
(74) *Attorney, Agent, or Firm* — Sheila A. Loggins

(57) ABSTRACT

Disclosed is the use of an effective photo-stabilizing amount of stabilizing agent (a) selected from a diphenylacrylate UV filter (a1), a benzylidene amphor derivative (a2), an organosiloxane comprising benzalemalonate groups (a3), a fluoren derivative (a4), and a naphthalene dicarboxylic acid derivative (a5) for improving the stability with respect to UV radiation of a cosmetic or dermatological composition comprising a UV filter combination of at least one dibenzoylmethane derivative (b) and of at least one specific amino-substituted 2-hydroxybenzophenone derivative (c).

8 Claims, No Drawings

PHOTO-STABLE COSMETIC OR DERMATOLOGICAL COMPOSITIONS

The present invention relates to the use of a specific stabilizing agent (a) for improving the stability with respect to UV radiation of a cosmetic or dermatological composition comprising a UV filter combination of at least one dibenzoylmethane derivative (b) and of at least one specific amino-substituted 2-hydroxybenzophenone derivative (c).

It has long been known that prolonged exposure to UV radiation can lead to the formation of erythemas or light dermatoses, as well as to an increased incidence of skin cancers or accelerated skin ageing.

Various sunscreen formulations have been proposed which include materials which are intended to counteract UV radiation, thereby inhibiting the said undesired effects on the skin.

A great number of compounds have been proposed for use as UV protectants in sunscreen formulations.

In this respect, a particular advantageous family of UV-A screening agents is currently composed of dibenzoyl methane derivatives and in particular 4-tert-butyl-4'-methoxydibenzoylmethane; this is because these derivatives exhibit a high intrinsic absorbance. Dibenzoylmethane derivatives are well known per se as screening agents actives in the UV-A region, and are disclosed in particular in FR-A-2 326 405, FR-A-2 440 933 and EP-A-0 114 607. Furthermore, 4-tert-butyl-4'-methoxydibenzoylmethane is currently offered for sale under the trademark of "Parsol 1789" by DSM.

Unfortunately, it is found that dibenzoylmethane derivatives are relatively sensitive to UV radiation (in particular UV-A radiation), AND more specifically, that they have an unfortunate tendency to more or less rapid decomposition under the effect of the latter. Thus, this substantial lack of photochemical stability of dibenzoylmethane derivatives with respect to UV radiation does not make it possible to guarantee constant protection during prolonged exposure to the sun, so that repeated sun screen applications at regular and frequent intervals have to be carried out by the user in order to obtain effective protection of the skin against UV radiation.

The photostabilization of dibenzoylmethane derivatives with respect to UV radiation constitutes a problem, which has not yet been solved until now in a completely satisfactory manner.

In U.S. Pat. No. 6,699,461 it is suggested to improve the photochemical stability of dibenzoyl-methane derivatives containing cosmetic or dermatological compositions with specific amino-substituted 2-hydroxybenzophenone derivatives. These compositions do not comprise p-methylbenzylidenecamphor.

Unfortunately, the addition of a 2-hydroxybenzophenone derivative in cosmetic or dermatological compositions photostabilizes the dibenzoylmethane derivative but simultaneously destabilizes the 2-hydroxybenzophenone derivative.

Surprisingly it was found, that the addition of specific amounts of a specific stabilizing agent will significantly improve the photostability of cosmetic or dermatological compositions comprising the combination of 2-hydroxybenzophenone and dibenzoylmethane derivatives.

Therefore, the present invention relates to the use of an effective photo-stabilizing amount of stabilizing agent (a) selected from
- a diphenylacrylate UV filter ($a_1$),
- a benzylidene camphor derivative ($a_2$),
- an organosiloxane comprising benzalemalonate groups ($a_3$),
- a fluoren derivative ($a_4$),
- a naphthalene dicarboxylic acid derivative ($a_5$)
- a natural occurring stabilizer ($a_8$); and
- a phenolic antioxidant ($a_7$);

for improving the stability with respect to UV radiation of a cosmetic or dermatological composition comprising a UV filter combination of at least one dibenzoylmethane derivative (b) and of at least one specific amino-substituted 2-hydroxybenzophenone derivative (c).

The diphenylacrylate UV filter ($a_1$) which is used in the present invention for the stabilization of cosmetic or dermatological composition is preferably selected from 2-ethylhexyl 2-cyano,3,3-diphenylacrylate which corresponds to the formula

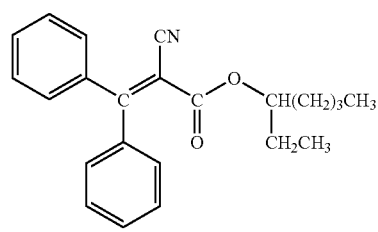

(1)

(Octocrylene).

Suitable benzylidene camphor derivatives ($a_2$) are disclosed in U.S. Pat. No. 5,605,680.

Preferably, p-methylbenzylidene camphor is used in the present invention as component ($a_2$).

The organosiloxane comprising benzalemalonate groups ($a_3$) preferably correspond to the formula

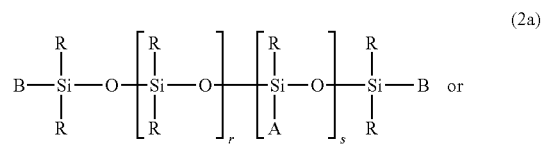

(2a)

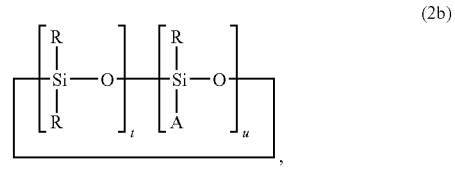

(2b)

wherein

R is $C_1$-$C_{10}$alkyl; phenyl; or 3,3,3-trifluoropropyl, at least 80% of the number of the R radicals being methyl radicals;

r is an integer from 0 to 200;

s is an integer from 0 to 50 u is an integer from 1 to 20;

t is an integer from 0 to 20; wherein t+u is equal to or greater than 3; and

A and/or B is a benzalmalonate radical.

A is preferably the radical of formula

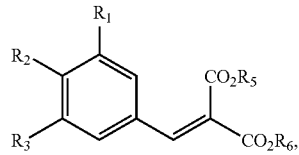
(2c)

wherein
$R_1$ and $R_2$ are each hydrogen; OH; trimethylsiloxy; $C_1$-$C_6$alkyl; $C_1$-$C_6$alkoxy; or a radical of the formula

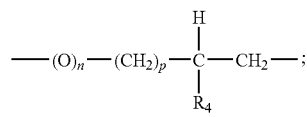
(2d)

with the proviso that one of the radicals $R_1$ and $R_2$ is the bivalent radical of formula (2d);
$R_3$ is hydrogen; $C_1$-$C_6$alkyl; or $C_1$-$C_6$alkoxy;
$R_4$ is hydrogen; or $C_1$-$C_4$alkyl; and
$R_5$ and $R_6$, independently from each other are $C_1$-$C_8$alkyl;
n is 0; or 1; and
p is a number from 0 to 5.

The fluoren derivative ($a_4$) is preferably selected from derivatives of cyano(9H-fluoren-9-ylidene)acetic acid, and diesters and polyesters of 9H-fluoren-ylidene malonic acid. These compounds are disclosed in US 2004/0057912.

Preferably, a 9-methylene-9H-fluoren derivative of formula

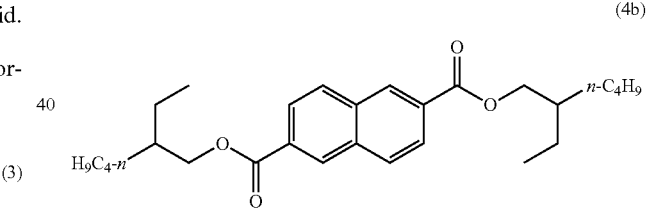
(3)

is used as component ($a_4$) in the present invention.

The naphthalene dicarboxylic acid derivatives ($a_5$) preferably correspond to the formula

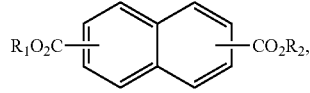
(4)

wherein
$R_1$ is a radical of formula

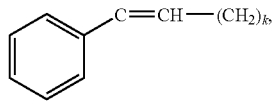
(4a)

k is a number from 1 to 13; and
$R_2$ is selected from the group consisting of a compound of formula (4a), or $C_1$-$C_{22}$alkyl.

The compounds are disclosed in WO 01/087528.
Preferably, compounds of the formula

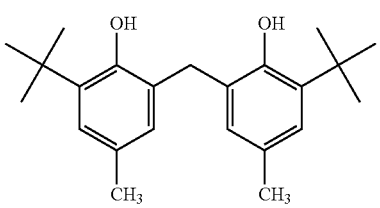
(4b)

are preferably used as component ($a_5$) in the present invention.

Dragosine, green tea concentrate and grape seed extract are typical representatives for stabilizers ($a_6$).

The phenolic antioxidants as listed in the Table below are useful stabilizer components ($a_7$) in the present invention:

TABLE 1

| compound of formula | |
| --- | --- |
| (AO-01) |  |

TABLE 1-continued
| compound of formula | |
|---|---|
| (AO-02) | 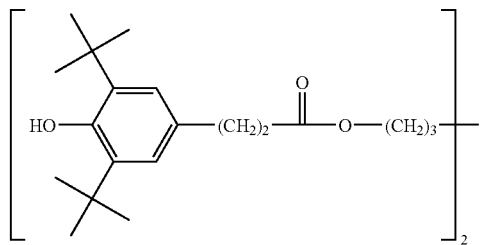 |
| (AO-03) | 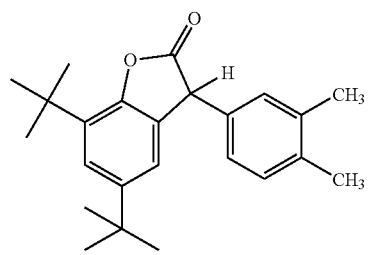 |
| (AO-04) | 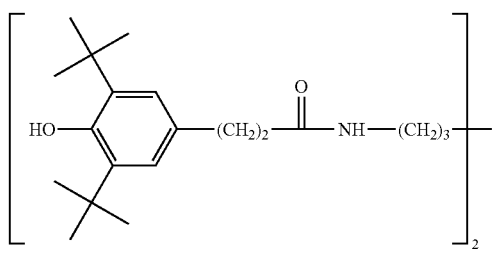 |
| (AO-05) | 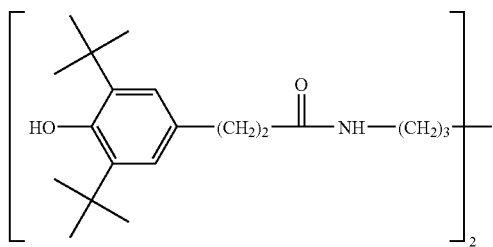 |
| (AO-06) | 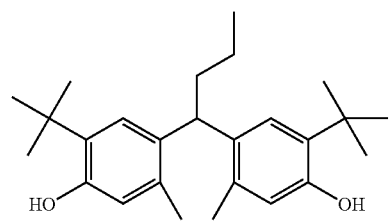 |

TABLE 1-continued
| compound of formula | |
|---|---|
| (AO-07) | 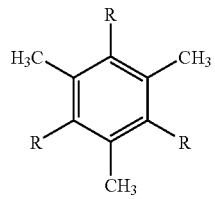 |
| | $R = $ 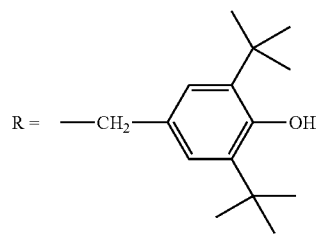 |
| (AO-08) | 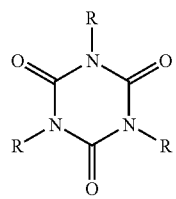 |
| | $R = $ 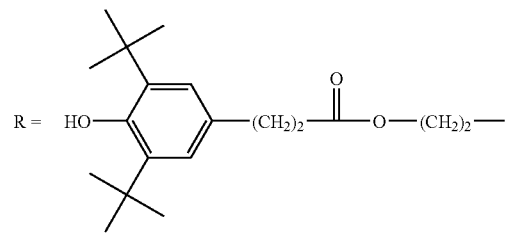 |
| (AO-09) | 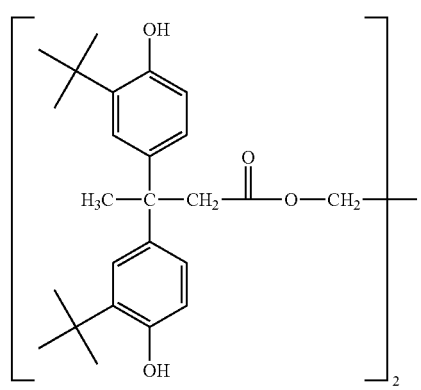 |
| (AO-10) | 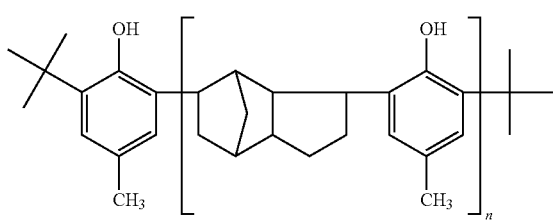
n = 1-3 |

TABLE 1-continued
| compound of formula | |
|---|---|
| (AO-11) | 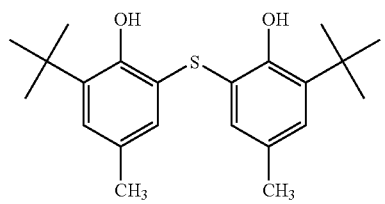 |
| (AO-12) | 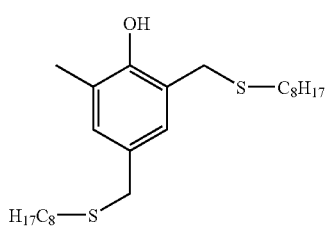 |
| (AO-13) | 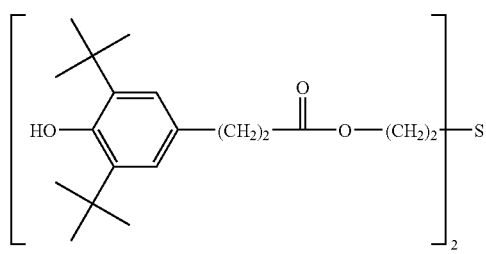 |
| (AO-14) | 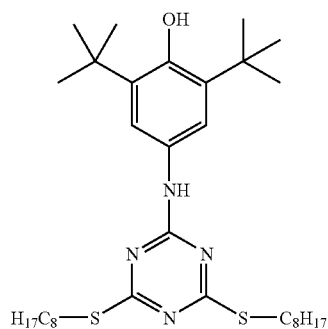 |
| (AO-15) | 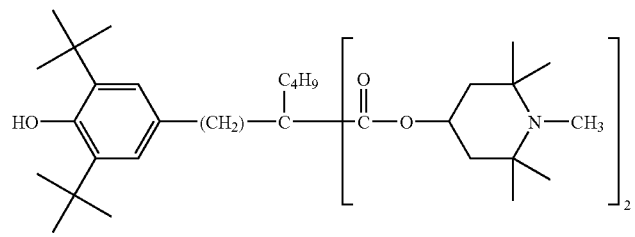 |
| (AO-16) | 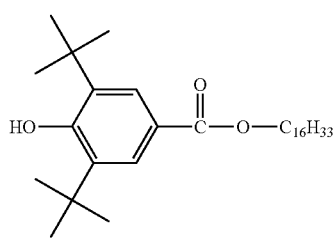 |

TABLE 1-continued
| compound of formula | |
|---|---|
| (AO-17) | 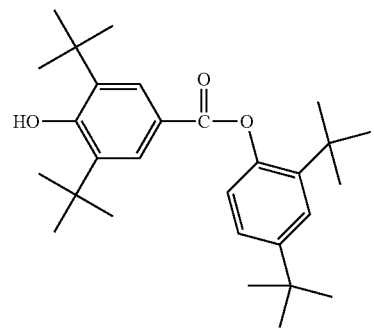 |
| (AO-18) | 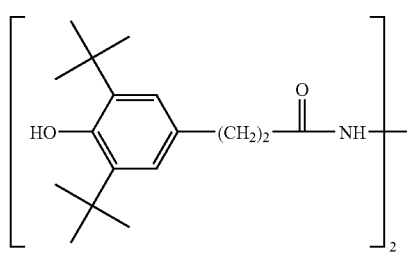 |
| (AO-19) | 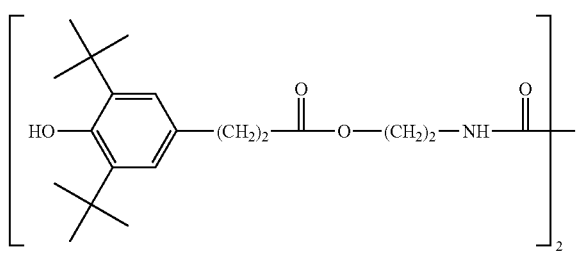 |
| (AO-20) | 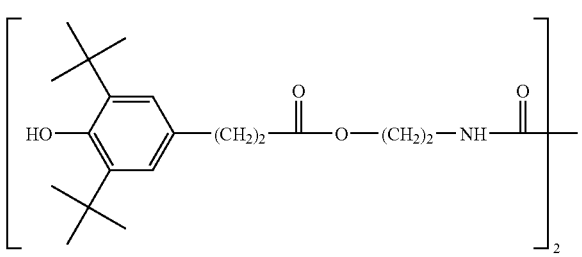 |
| (AO-21) | 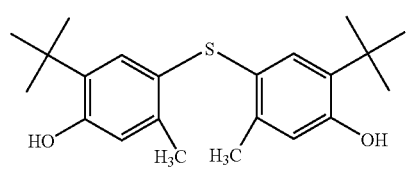 |
| (AO-22) | 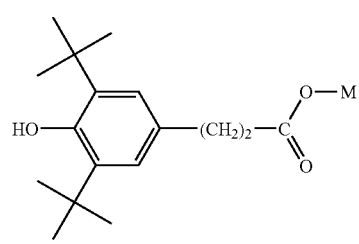 |
M = H, ammonium, alkali TABLE 1-continued

| compound of formula | |
|---|---|
| (AO-23) | 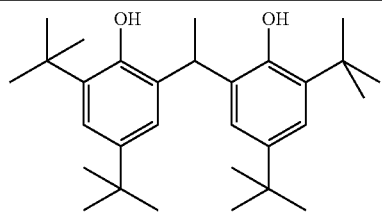 |
| (AO-24) | 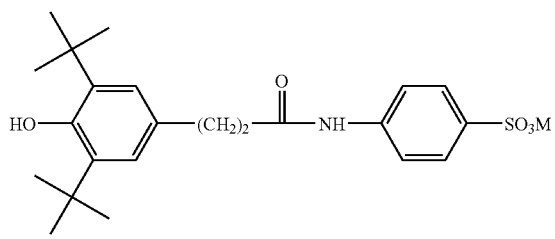<br>M = H, Na |
| (AO-25) | 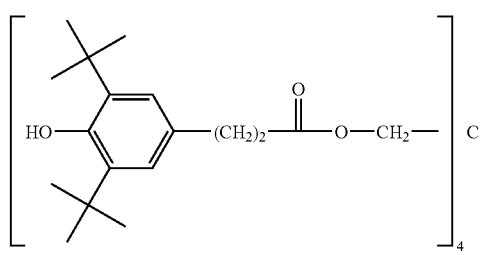 |
| (AO-26) | 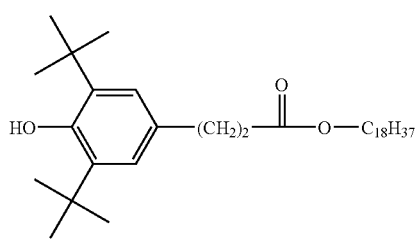 |
| (AO-27) | 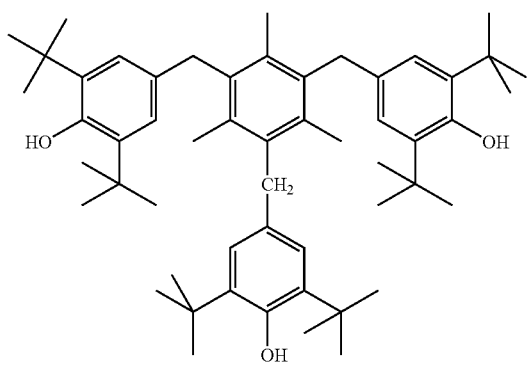 |

Furthermore, the stabilizers disclosed in the following references, can advantageously be used in the present composition: US 2004057914; WO 2003039506; DE 10141473; WO 2003020317; WO 2003020224; US 2002197285; EP 1127569; EP 1127568; FR 2801209; FR 2801207; "A new photostabilizer for full spectrum sunscreens", Cosmetics & Toiletries (2000), 115(6), p. 37-45; U.S. Pat. No. 5,993,789.

The stabilizer compounds corresponding to components $(a_1)$ to $(a_7)$ are used as single components or can be used as mixtures in the present composition consisting of two, three, four or even more of the components $(a_1)$ to $(a_7)$.

The term "effective amount of a stabilizer" in accordance with the present invention is understood to mean an amount sufficient to produce a noteworthy and significant improvement in the photostability of the UV filter combination dibenzoylmethane derivative (b) and amino-substituted 2-hydroxybenzophenone derivative (c). This minimum amount of photostabilizing agent to be employed, which can vary depending on the nature of the cosmetically acceptable vehicle used for the composition, can be determined without any difficulty by means of a conventional test for measuring photostability.

Preferably, this UV filter is used in the cosmetic or dermatological composition in a concentration range from 1 to 10% b.w. of the cosmetic composition.

The 2-hydroxybenzophenone derivative according to component (c) of the cosmetic or dermatological composition preferably corresponds to formula

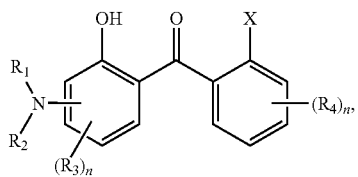

(5)

wherein
- $R_1$ and $R_2$, independently from each other are hydrogen; $C_1$-$C_{30}$alkyl; $C_2$-$C_{10}$alkenyl; $C_3$-$C_{10}$ cycloalkyl; or $C_3$-$C_{10}$cycloalkenyl; or
- $R_1$ and $R_2$ together form, with the nitrogen atom to which they are bonded, a 5- or 6-membered heterocyclic ring member;
- $R_3$ and $R_4$, independently from each other, are each $C_1$-$C_{20}$alkyl; $C_2$-$C_{10}$alkenyl; $C_3$-$C_{10}$cycloalkyl; $C_3$-$C_{10}$cycloalkenyl; $C_1$-$C_{12}$alkoxy; $(C_1$-$C_{20})$alkoxycarbonyl; $C_1$-$C_{12}$alkylamino; di($C_1$-$C_{12}$)alkylamino; an aryl or a heteroaryl radical which is optionally substituted; or a water-solubilizing substituent selected from a carboxylate group, a sulfonate group or an ammonium residue;
- X is hydrogen; —COOR$_5$; or —CONR$_6$R$_7$;
- $R_5$, $R_6$ and $R_7$, independently from each other, are hydrogen; $C_1$-$C_{20}$alkyl; $C_2$-$C_{10}$alkenyl; $C_3$-$C_{10}$cycloalkyl; $C_3$-$C_{10}$cycloalkenyl, —(Y'O)$_o$—Z'; or aryl;
- Y' is —(CH$_2$)$_2$—; —(CH$_2$)$_3$—; —(CH$_2$)$_4$—; or —CH—(CH$_3$)—CH$_2$—;
- Z' is —CH$_2$—CH$_3$; —CH$_2$—CH$_2$CH$_3$; —CH$_2$CH$_2$—CH$_2$—CH$_3$ or —CH(CH$_3$)—CH$_3$;
- n is an integer from 0 to 3; and
- o is an integer from 1 to 2.

$C_1$-$C_{20}$alkyl is for example methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, n-hexyl, 1,1-dimethylpropyl, 1,2-dimethyl propyl, 1-methyl-pentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

$C_2$-$C_{10}$alkenyl is for example: vinyl, n-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

$C_1$-$C_{12}$alkoxy is for example methoxy, ethoxy, n-propoxy, n-butoxy, n-pentoxy, 1-methyl-propoxy, 3-methylbutoxy, 2,2-dimethylpropoxy, 1-methyl-1-ethylpropoxy, octoxy, 2-methylpropoxy, 1,1-dimethylpropoxy, hexoxy, heptoxy or 2-ethylhexoxy.

$C_3$-$C_{10}$cycloalkyl is for example cyclopropyl, cyclobutyl, cyclopentyl, cyclohexyl, cycloheptyl, 1-methylcyclo-propyl, 1-ethylcyclopropyl, 1-propylcylopropyl, 1-butylcyclopropyl, 1-pentyl-cyclopropyl, 1-methyl-1-butylcyclopropyl, 1,2-dimethylcyclopropyl, 1-methyl-2-ethylcyclopropyl, cyclooctyl, cyclononyl or cyclodecyl.

$C_3$-$C_{10}$cycloalkenyl is for example cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals can comprise one or more substituents (preferably from 1 to 3) and are selected, for example, from halogen, such as chlorine, fluorine or bromine; cyano; nitro; amino; $C_1$-$C_4$alkylamino; di($C_1$-$C_4$)alkylamino; $C_1$-$C_4$alkyl; $C_1$-$C_4$alkoxy; or hydroxyl. They can also comprise from 1 to 3 heteroatoms, such as sulphur, oxygen or nitrogen, the free valencies of which can be occupied by a hydrogen or a $C_1$-$C_4$alkyl radical.

The aryl groups are preferably chosen from phenyl or naphthyl rings which can comprise one or more substituents (preferably from 1 to 3) chosen, for example, from halogen, such as chlorine, fluorine or bromine; cyano; nitro; amino; $C_1$-$C_4$alkylamino; di($C_1$-$C_4$)alkylamino; $C_1$-$C_4$alkyl; $C_1$-$C_4$alkoxy; or hydroxyl.

Preference is more particularly given to phenyl, methoxyphenyl and naphthyl.

The heteroaryl groups generally comprise one or more heteroatoms chosen from sulphur, oxygen or nitrogen.

The water-solubilizing groups are, for example, carboxylate or sulphonate groups and more particularly their salts with physiologically acceptable cations, such as alkali metal salts or tri-alkylammonium salts, such as tri(hydroxyalkyl)ammonium or 2-methylpropan-1-ol-2-ammonium salts. Mention may also be made of ammonium groups, such as alkylammoniums, and their salified forms with physiologically acceptable anions.

Mention may in particular be made, as examples of the 5- or 6-membered heterocyclic ring member formed by the $R_1$ and $R_2$ with the nitrogen atom, of pyrrolidine or piperidine.

The amino groups can be attached to the benzene ring in the ortho, meta or para position with respect to the carbonyl radical and more preferably in the para position.

Preferably, the 2-hydroxybenzophenone derivative (b) in the cosmetic or dermatological composition corresponds to formula

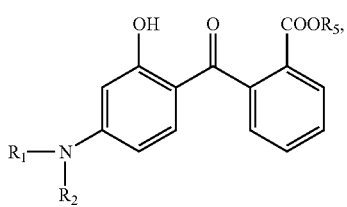

(6)

wherein

R$_1$ and R$_2$, independently from each other, are hydrogen; or C$_1$-C$_8$alkyl; or together form, with the nitrogen atom to which they are bonded, a 5- or 6-membered heterocyclic ring member; and R$_5$ is hydrogen; C$_1$-C$_5$alkyl; or a C$_3$-C$_6$cycloalkyl.

Most preferably the compound of formla

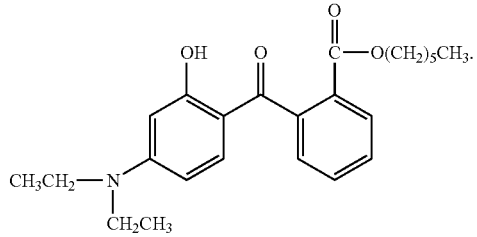

(7)

is used as component (c) in the cosmetic or dermatological composition.

The dibenzoylmethane derivatives according to component (b) according to the present invention are products which are already well known per se and which are disclosed in particular in FR 2,326,405, FR 2,440,933 and EP 0,114,607, the teachings of which documents are, insofar as they affect the actual definition of these products, entirely included by way of references in the present description.

According to the present invention, it is possible, of course, to employ one or more dibenzoylmethane derivatives.

Examples of dibenzoylmethane derivatives (b) are: 2-methyldibenzoylmethane; 4-methyldibenzoylmethane; 4-isopropyldibenzoylmethane; 4-tert-butyldibenzoylmethane; 2,4-dimethyldibenzoyl methane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoyl methane; 2-methyl-5-tert-butyl-4'-methoxydibenzoylmethane; 2,4-dimethyl-4'-methoxydibenzoylmethane; or 2,6-dimethyl-4-tert-butyl-4'-methoxydibenzoylmethane.

Preference is very particularly given according to the present invention, among the above-mentioned dibenzoylmethane derivatives, to the use of 4-tert-butyl-4'-methoxydibenzoylmethane, in particular that offered for sale under the trademark of "Parsol 1789" by Hoffmann-LaRoche, this screening agent corresponding to the following formula

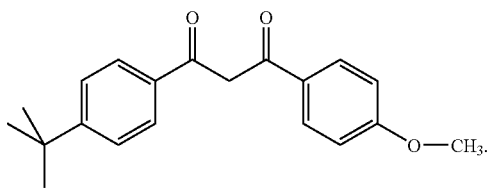

(8)

Another preferred dibenzoylmethane derivative according to the present invention is 4-isopropyldibenzoylmethane, a screening agent sold under the name of "Eusolex 8020" by Merck and corresponding to the formula

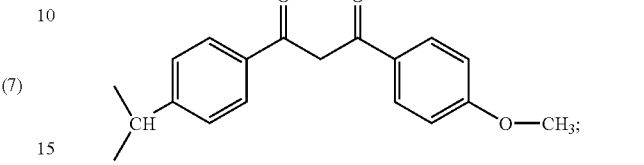

(9)

or 4-Ethylhexyl-4'Methoxydibenzoylmethane corresponding to formula

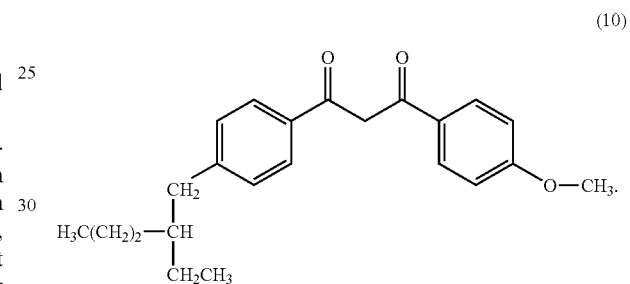

(10)

The dibenzoylmethane derivative (b) is present in the compositions in accordance with the invention at contents preferably ranging from 0.3 to 10% by weight and more preferably from 0.5 to n10% by weight and more particularly from 0.5 to 8% by weight, with respect to the total weight of the composition.

The cosmetic or dermatological composition comprising at least 1 to 10% b.w of a stabilizing agent (a) selected from a diphenylacrylate UV filter (a$_1$), a benzylidene cmphor derivative (a$_2$), an organosiloxane comprising benzalemalonate groups (a$_3$), a fluoren derivative (a$_4$), and a naphthalene dicarboxylic acid derivative (a$_5$);

2.0 to 5% b.w of a dibenzoylmethane derivative (b); and 0.3 to 10% b.w. of an amino-substituted 2-hydroxybenzophenone derivative (c);

is a further object of the present invention.

The cosmetic or dermatological compositions according to the present invention comprising components (a), (b) and (c) are particularly suitable as UV filters, i.e. for protecting UV-sensitive organic materials, in particular the skin and hair of humans and animals, from the harmful effects of UV radiation. These compositions are therefore suitable as sunscreens in cosmetic, pharmaceutical and veterinary medical preparations.

The cosmetic formulations or dermatological compositions according to the present invention may additionally contain one or more than one further UV filter as listed in Table 1.

TABLE 2

Suitable UV filter substances and adjuvants which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2'-4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethlamino)benzoate | 21245-02-3 |
| 31 | 2-ethylhexyl 4-methoxycinnamate; octyl methoxy cinnamate | 5466-77-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis-{[4-(2-ethylhexyloxy)-2-hydroxy]-phenyl}-6-(4-methoxy-phenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]carbonyl]phenyl]-amino]1,3,5-triazine-2,4-diyl]diimino]bis-, bis(2-ethylhexyl)ester; di-ethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 52 | Benzoic acid, 2-[4-(diethylamino)-2-hydroxybenzoyl]-, hexyl ester; Uvinul a plus | 302776-68-7 |
| 53 | 1-Dodecanaminium, N-[3-[[4-(dimethylamino)benzoyl]amino]propyl]-N,N-dimethy-, salt with with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-a-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |

TABLE 2-continued

Suitable UV filter substances and adjuvants which can be additionally used with the UV absorbers according to the present invention

| No. | Chemical Name | CAS No. |
|---|---|---|
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine, 2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 67 | Merocyanine derivaatives as described in WO 2004006878 and in IPCOM000022279D | |
| 68 | *(chemical structure)* | |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |

The cosmetic or dermatological preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester etc.

The stabilizing agents $(a_1)$-$(a_7)$ can also be used for stabilizing the specific amino-substituted 2-hydroxybenzophenone derivative (c). This is another object of the present invention.

Cosmetic or pharmaceutical preparations contain from 0.05-40% by weight, based on the total weight of the composition, of the UV filter components (a), (b) and (c).

Preference is given to the use of mixing ratios of the UV filter components (a), (b) and (c) according to the present invention and optionally further light-protective agents (as described in Table 2) from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase the UV absorption.

The UV filter compounds (a), (b) and (c) according to the present invention as well as the additional filters listed in Table 1 can be used either in the dissolved state (soluble organic filters, solubilized organic filters) or in the micronised state (nanoscalar organic filters, particulate organic filters, UV-absorber pigments).

Any known process suitable for the preparation of microparticles can be used for the preparation of the micronised UV absorbers, for example wet-milling, wet-kneading, spray-drying from a suitable solvent, by the expansion according to the RESS process (Rapid Expansion of Supercritical Solutions) of supercritical fluids (e.g. $CO_2$) in which the UV filter or filters is/are dissolved, by reprecipitation from suitable solvents, including supercritical fluids (GASR process=Gas Anti-Solvent Recrystallisation/PCA process=Precipitation with Compressed Anti-solvents).

As milling apparatus for the preparation of the micronised organic UV absorbers there may be used, for example, a jet mill, ball mill, vibratory mill or hammer mill, preferably a high-speed mixing mill. The grinding is preferably carried out with a grinding aid.

As kneading apparatus for the preparation of the micronised organic UV absorbers examples are typically sigma-hook batch kneaders but also serial batch kneaders (IKA-Werke) or continuous kneaders (Contiuna from Werner and Pfleiderer).

Useful low molecular weight grinding aids for the micronizing processes mentioned above are surfactants and emulsifies.

Useful polymeric grinding aids for water dispersion are cosmetically acceptable water soluble polymers with Mn>500 g/mol, for example acrylates (Salcare types), modified or non-modified polysaccharides, polyglucosides or xanthan gum. Furthermore an alkylated vinylpyrrolidone polymer, a vinylpyrrolidone/vinyl acetate copolymer, an acyl glutamate, an alkyl polyglucoside, ceteareth-25 or a phospholipid may be used. Oil dispersions may contain cosmetically acceptable waxy polymers or natural waxes as polymeric grinding aid in order to adjust viscosity during and after processing. Examples of other useful polymeric grinding aids are disclosed below in the chapter "polymers".

Useful solvents for the grinding process are water, brine, (poly-)ethylenglycol, glycerine or cosmetically acceptable oils. Other useful solvents are disclosed below in the chapters "esters of fatty acids", "natural and synthetic triglycerides including glyceryl esters and derivatives", "perlescent waxes", "hydrocarbon oils" and "silicones or siloxanes".

The micronised UV absorbers so obtained usually have an average particle size from 0.02 to 2, preferably from 0.03 to 1.5, and more especially from 0.05 to 1.0 micrometer.

The UV absorbers used in the cosmetic or dermatological compositions of the present invention can also be used as dry substrates in powder form. For that purpose the UV absorbers are subjected to known grinding methods, such as vacuum atomization, countercurrent spray-drying etc.

The UV absorbers used in the cosmetic or dermatological compositions of the present invention can also be used in specific carriers for cosmetics, for example in solid lipid nano-particles (SLN) or in inert sol-gel microcapsules wherein the UV absorbers are encapsulated (Pharmazie, 2001 (56), p. 783-786).

The cosmetic or dermatological preparations may be, for example, creams, gels, lotions, alcoholic and aqueous/alcoholic solutions, emulsions, wax/fat compositions, stick preparations, powders or ointments. In addition to the abovementioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of a UV absorber composition comprising the components (a), (b) and (c), from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or dermatological preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, natural or synthetic triglycerides including glyceryl esters and derivatives, pearlescent waxes, hydrocarbon oils, silicones or siloxanes (organosubstituted polysiloxanes), fluorinated or perfluorinated oils, mulsifiers, super-fatting agents, surfactants, consistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, and polymeric beads or hollow spheres as SPF enhancers.

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may exist in a wide variety of presentation forms, for example:
- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up,
- in the form of a stick,
- in the form of a spray (spray with propellent gas or pump-action spray) or an aerosol,
- in the form of a foam, or
- in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber composition according to the invention comprising the components (a), (b) and (c), 12.0% by weight of sodium laureth-2-sulfate, 4.0% by weight of cocamidopropyl betaine, 3.0% by weight of sodium chloride, and water ad 100%.

Examples of Cosmetic and Pharmaceutical Preparations (X=Preferred Combinations)

| Ingredients | O/W systems: | | | | | | | |
|---|---|---|---|---|---|---|---|---|
| | 1 | 2 | 3 | 4 | 5 | 6 | 7 | 8 |
| Emulsifiers | | | | | | | | |
| Potassium Cetyl Phosphate 2-5% | X | | | | | | | |
| Cetearyl Alcohol/Dicetyl Phosphate/Ceteth-10 Phosphate 2-6% | | X | | | | | | |
| Sodium Stearyl Phtalamate 1-2% | | | X | | | | | |
| Cetearyl Alcohol/Behentrimonium Methosulfate 1-5% | | | | X | | | | |
| Quaternium-32 1-5% | | | | | X | | | |
| Dimethicone copolyol/Caprylic/Capric Triglyceride (1-4%) | | | | | | X | | |
| Steareth-2/Steareth-21 2-5% | | | | | | | X | |
| Polyglyceryl Methyl Glucose Distearate 1-4% | | | | | | | | X |
| Lipophilic emollient/dispersant oil 15-20% | X | X | X | X | X | X | X | X |
| Fatty Alcohols and/or Waxes 1-5% | X | X | X | X | X | X | X | X |
| Thickeners (water swellable thickeners) 0.5-1.5% | X | X | X | X | X | X | X | X |
| Preservatives 0.5-1% | X | X | X | X | X | X | X | X |
| Chelating agents (such as EDTA) 0-0.2% | X | X | X | X | X | X | X | X |
| Antioxidants 0.05-0.2% | X | X | X | X | X | X | X | X |
| Water deionized Qs 100% | X | X | X | X | X | X | X | X |
| Perfume oils 0.1-0.4% | X | X | X | X | X | X | X | X |
| UV-absorber composition comprising components (a), (b) and (c) according to the invention; 0.1-20% | X | X | X | X | X | X | X | X |
| UV-absorber as described in Table 2; 0-30% | X | X | X | X | X | X | X | X |

| Ingredients | W/O systems | | | | |
|---|---|---|---|---|---|
| | 1 | 2 | 3 | 4 | 5 |
| Emulsifiers | X | X | X | X | X |
| Polyglyceryl-2 Dipolyhydroxystearate 2-4% | X | X | X | X | X |
| PEG-30 Dipolyhydroxystearate 2-4% | | | X | | |
| Rapeseed Oil Sorbitol Esters 1-5% | | X | | | |
| PEG-45/Dodecyl Glycol Copolymer 1-5% | | | | X | |
| Sorbitan Oleate/Polycerol-3 ricinoleate 1-5% | | | | | X |
| Lipophilic emollient/dispersant oil 10-20% | X | X | X | X | X |
| Fatty Alcohols and/or Waxes 10-15% | X | X | X | X | X |
| Electrolytes (NaCl, MgSO$_4$) 0.5-1% | X | X | X | X | X |
| Polyol phase (Propylene glycol, glycerin) 1-8% | X | X | X | X | X |
| Preservatives 0.3-0.8% | X | X | X | X | X |
| Perfume oils 0.1-0.4% | X | X | X | X | X |
| Chelating agents (such as EDTA) 0-0.2% | X | X | X | X | X |
| Antioxidants 0.05-0.2% | X | X | X | X | X |
| Water deionized Qs 100% | X | X | X | X | X |
| UV-absorber composition comprising components (a), (b) and (c) according to the invention; 0.1-20% | X | X | X | X | X |
| UV-absorber as described in Table 2; 0-30% | X | X | X | X | X |

| Ingredients | W/Silicone systems | | | |
|---|---|---|---|---|
| | 1 | 2 | 3 | 4 |
| Dimethicone Copolyol/Cyclomethicone 5-10% | X | | X | |
| Laurylmethicone Copolyol 5-10% | | X | | X |

W/Silicone systems

| Ingredients | 1 | 2 | 3 | 4 |
|---|---|---|---|---|
| Cyclopentasiloxane 15-25% | X | | | X |
| Dimethicone 15-25% | | X | X | |
| Dimethicone/Vinyldimethicone Crosspolymer 1-10% | X | X | X | X |
| Humectant/polyols (Propylene glycol, glycerin . . . ) 2-8% | X | X | X | X |
| Chelating agents (such as EDTA) 0-0.2% | X | X | X | X |
| Antioxidants 0.05-0.2% | X | X | X | X |
| Preservatives 0.3-0.8% | X | X | X | X |
| Perfume oils 0.1-0.4% | X | X | X | X |
| Water deionized Qs 100% | X | X | X | X |
| UV-absorber composition comprising components (a), (b) and (c) according to the invention; 0.1-20% | X | X | X | X |
| UV-absorber as described in Table 2; 0-30% | X | X | X | X |

Multiple emulsions

| Ingredients | 1 | 2 | 3 | 4 | 5 | 6 | 7 | 8 | 9 | 10 | 11 | 12 |
|---|---|---|---|---|---|---|---|---|---|---|---|---|
| PEG-30 Dipolyhydroxystearate (2-6%) | X | | | | | | | | | X | | X |
| Cetyl Dimethicone Copolyol 1-3% | | X | | | | | | | X | | | |
| PEG-30 Dipolyhydroxystearate/Steareth-2/Steareth-21 4-6% | | | X | | | | | X | | | | |
| Polyglyceryl-2 Dipolyhydroxystearate 1-3% | | | | X | | | X | | | | | |
| Polyglyceryl-6 Ricinoleate 1-3% | | | | | X | X | | | | | X | |
| Oil phase 15-30% | | | | | | | | | | | | |
| Fatty acid esters | X | X | X | X | X | | | | | | X | X |
| Natural and synthetic Triglycerides | | | | | | X | X | X | X | X | X | X |
| Hydrocarbon oils | X | X | X | X | X | | | | | | X | X |
| Silicone oils | | | | | | X | X | X | X | X | X | X |
| Preservatives 0.3-0.8% | X | X | X | X | X | X | X | X | X | X | X | X |
| Water Deioniz. qs 100% | X | X | X | X | X | X | X | X | X | X | X | X |
| Sorbitan Stearate/Sucrose Cocoate 3-7% | X | | | | | | | | X | | | X |
| Sucrose Laurate 3-7% | | X | | X | | | X | | | X | | |
| Poloxamer 407 3-7% | | | X | | X | | | X | | | | |
| Polyoxyethylene(20)Sorbate Monoleate 3-5% | | | | | X | X | | | | X | | |
| Primary emulsion W1/O 50% | X | X | X | X | X | X | X | X | X | X | X | X |
| Thickeners (water swellable polymers) 0.3-1% | X | X | X | X | X | X | X | X | X | X | X | X |
| Water deionized Qs 100% | X | X | X | X | X | X | X | X | X | X | X | X |
| Perfume oils 0.1-0.4% | X | X | X | X | X | X | X | X | X | X | X | X |
| UV-absorber composition comprising components (a), (b) and (c) according to the invention; 0.1-20% | X | X | X | X | X | X | X | X | X | X | X | X |
| UV-absorber as described in Table 2; 0-30% | X | X | X | X | X | X | X | X | X | X | X | X |

O1/W/O2 emulsions

| Ingredients | 1 | 2 | 3 | 4 | 5 | 6 | 7 | 8 |
|---|---|---|---|---|---|---|---|---|
| Primary emulsion O1/W | | | | | | | | |
| PEG-60 Hydrogenated Castor Oil 25% | X | | | X | X | | | X |
| Steareth-25 25% | | X | X | | | X | X | |
| Oil phase 75% | | | | | | | | |
| Fatty acid esters | X | | X | | | | | |
| Natural and synthetic Triglycerides | | X | | X | | | | |
| Hydrocarbon oils | | | | | X | | X | |
| Silicone oils | | | | | | X | | X |
| Preservatives 0.3-0.8% | X | X | X | X | X | X | X | |
| Water deionized Qs 100% | X | X | X | X | X | X | X | |
| Nonionic multifunctional W/O emulsifier 2-5% | X | X | X | X | X | X | X | |
| Waxes 1-5% | X | X | X | X | X | X | X | |
| Oil phase 20-30% | X | X | X | X | X | X | X | |
| Silicone oils | | | | | | | | |
| Primary emulsion O1/W 15% | X | X | X | X | X | X | X | |
| Electrolytes (NaCl, MgSO$_4$) 0.1-0.5% | X | X | X | X | X | X | X | |
| Water deionized Qs 100% | X | X | X | X | X | X | X | |
| Perfume oils 0.1-0.4% | X | X | X | X | X | X | X | |

| O1/W/O2 emulsions | | | | | | | | |
|---|---|---|---|---|---|---|---|---|
| Ingredients | 1 | 2 | 3 | 4 | 5 | 6 | 7 | 8 |
| UV-absorber composition comprising components (a), (b) and (c) according to the invention; 0.1-20% | X | X | X | X | X | X | X | X |
| UV-absorber as described in Table 2; 0-30% | X | X | X | X | X | X | X | X |

| Microemulsions | | | | | | | | | | |
|---|---|---|---|---|---|---|---|---|---|---|
| Ingredients | 1 | 2 | 3 | 4 | 5 | 6 | 7 | 8 | 9 | 10 |
| PEG-8 Caprylic/Capric Glycerides 10-25% | X | | | X | X | | | X | X | |
| PPG-5-ceteth-20 10-25% | | X | X | | | X | X | | | X |
| Polyglyceryl-6 Isostearate 5-15% | X | | X | | | | | | | |
| Polyglyceryl-3 Diisostearate 5-15% | | X | | X | | | | | | |
| Polyglyceryl-6 Dioleate 5-15% | | | | | X | | X | | | |
| PPG-10 Cetyl Ether 5-15% | | | | | | X | | X | | |
| Ethoxydiglycol 5-15% | | | | | | | | | X | X |
| Oil phase 10-80% | X | X | X | X | X | X | X | X | X | X |
| Isostearyl Benzoate | X | X | X | X | X | X | X | X | X | X |
| Isostearyl Isostearate | X | X | X | X | X | X | X | X | X | X |
| PEG-7 Glyceryl Cocoate | X | X | X | X | X | X | X | X | X | X |
| Cyclomethicone | X | X | X | X | X | X | X | X | X | X |
| Polyalcohols/Humectants 1-10% | X | X | X | X | X | X | X | X | X | X |
| Preservatives 0.3-0.8% | X | X | X | X | X | X | X | X | X | X |
| Perfume oils 0.1-0.4% | X | X | X | X | X | X | X | X | X | X |
| Water Deioniz. qs 100% | X | X | X | X | X | X | X | X | X | X |
| UV-absorber composition comprising components (a), (b) and (c) according to the invention; 0.1-20% | X | X | X | X | X | X | X | X | X | X |
| UV-absorber as described in Table 2; 0-30% | X | X | X | X | X | X | X | X | X | X |

| O/W Spray emulsions | | | | | | |
|---|---|---|---|---|---|---|
| Ingredients | 1 | 2 | 3 | 4 | 5 | 6 |
| Alkyl Phosphates 0.1-5% | X | | | X | X | |
| Glucosidic derivatives 0.1-5% | | X | X | | | X |
| Solubilisants | | | | | | |
| Ethoxylated Glyceryl ethers 0.1-1% | X | | X | | | |
| Polysorbates 0.1-1% | | X | | X | | |
| Ethoxylated Oleyl ethers 0.1-1% | | | | | X | X |
| PVP/VA Copolymer 1-10% | X | | X | | X | |
| PVM/MA Copolymer 1-10% | | X | | X | | X |
| Oil phase 5-20% | X | X | X | X | X | X |
| Natural oils (Meadowfoam, Jojoba, Macadamia ...) | X | X | X | X | X | X |
| Fatty acids esters | X | X | X | X | X | X |
| Mineral oils | X | X | X | X | X | X |
| Silicone oils | X | X | X | X | X | X |
| Alcohol 0-50% | X | X | X | X | X | X |
| Thickeners 0.1-0.5% | X | X | X | X | X | X |
| Polyacrylates | X | X | X | X | X | X |
| Aluminium/Magnesium Silicates | X | X | X | X | X | X |
| Gums | X | X | X | X | X | X |
| Neutralizing agents 0-1% | X | X | X | X | X | X |
| Polyalcohols/Humectants 1-5% | X | X | X | X | X | X |
| Chelating agents (such as EDTA) 0-0.2% | X | X | X | X | X | X |
| Antioxidants 0.05-0.2% | X | X | X | X | X | X |
| Water Deioniz. qs 100% | X | X | X | X | X | X |
| Perfume oils 0.1-0.5% | X | X | X | X | X | X |
| Preservatives 0.4-1% | X | X | X | X | X | X |
| UV-absorber composition comprising components (a), (b) and (c) according to the invention; 0.1-20% | X | X | X | X | X | X |
| UV-absorber as described in Table 2; 0-30% | X | X | X | X | X | X |

| G - Aqueous | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Thickeners | | | | | | | | | | | | |
| Natural Thickener 1-5% | X | | | | | X | X | | | | | X |
| Semi-synthetic Thickener 1-5% | | X | | | X | | | X | | | X | |
| Synthetic Thickener 0.3-1.3% | | | X | X | | | | | X | X | | |
| Neutralizing Agents 0.5-1.5% | X | X | X | X | X | X | X | X | X | X | X | X |
| Polyols - Humectants 5-50% | X | X | X | X | X | X | X | X | X | X | X | X |
| Polyquaternium series 1-5% | X | X | X | | | | X | X | X | | | |
| PVM/MA Copolymer 1-5% | | | | X | X | X | | | | X | X | X |
| Preservatives 0.5-1% | X | X | X | X | X | X | X | X | X | X | X | X |

-continued

| G - Aqueous | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Chelating Agents (as EDTA) <0.1% | X | X | X | X | X | X | X | X | X | X | X | X |
| Water Deioniz. qs 100% | X | X | X | X | X | X | X | X | X | X | X | X |
| Perfume oils 0.05-0.4% | X | X | X | X | X | X | X | X | X | X | X | X |
| Ethoxylated Glyceryl ethers 0.1-5% | X | X | X | | | | | | | | | |
| Polysorbates 0.1-5% | | | | X | X | X | | | | | | |
| Ethoxylated Oleyl ethers 0.1-5% | | | | | | | | X | X | X | X | X |
| UV-absorber composition comprising components (a), (b) and (c) according to the invention; 0.1-20% | X | X | X | X | X | X | X | X | X | X | X | X |
| UV-absorber as described in Table 2; 0-30% | X | X | X | X | X | X | X | X | X | X | X | X |

| Oleogels | | | | | | | | | | | |
|---|---|---|---|---|---|---|---|---|---|---|---|
| Ingredients | 1 | 2 | 3 | 4 | 5 | 6 | 7 | 8 | 9 | 10 |
| Hydrogenated Lecithin 1-10% | X | | | | | | | | X | |
| Silica Dimethyl Silylate 1-10% | | X | | | | | | | X | |
| Silica 1-5% | | | X | | | | | X | | |
| $C_{24-28}$ Alkyl Dimethicone 1-5% | | | | X | | | X | | | |
| Aluminium or Magnesium Stearate 1-5% | | | | | X | X | | | | |
| Polyols - Humectants 5-70% | X | X | X | X | X | X | X | X | X | X |
| Oil phase 20-90% | | | | | | | | | | |
| Dicaprylyl Ether | X | | | | | X | | X | | |
| Phenyl Trimethicone | | X | | | | | | X | | |
| Hydrogenated Polyisobutene | | | | X | | | | | | |
| Isopropyl Isostearate | | | | X | | | | | X | |
| Oleogel basis (Mineral oil and hydrogenated Butylene/Ethylene or Ethylene/Propylene Styrene Copolymer) | | | | | | X | | | | X |
| Silicone wax 1-10% | X | X | X | X | X | X | X | X | X | |
| Dimethiconol Behenate | X | X | X | X | X | X | X | X | X | |
| Dimethiconol Stearate | X | X | X | X | X | X | X | X | X | |
| Perfume oils 0.1-0.5% | X | X | X | X | X | X | X | X | X | |
| Antioxidants 0.05-0.2% | X | X | X | X | X | X | X | X | X | |
| UV-absorber composition comprising components (a), (b) and (c) according to the invention; 0.1-20% | X | X | X | X | X | X | X | X | X | |
| UV-absorber as described in Table 2; 0-30% | X | X | X | X | X | X | X | X | X | |

| Light/dry cosmetic oils | | | | |
|---|---|---|---|---|
| Ingredients | 1 | 2 | 3 | 4 |
| Hydrocarbon oils 30-70% | X | | | X |
| Fatty acid esters branched or not 10-50% | | X | X | |
| Silicones/Siloxanes 0-10% | X | | X | |
| Perfluorinated oils and Perfluoroethers 0-10% | | X | | X |
| Viscosifying agents 0-10% | X | X | X | X |
| Esters of long chain acids and alcohols 0-2% | X | X | X | X |
| Antioxidants 0.1-1% | X | X | X | X |
| Solubilisants/dispersing agents 0-5% | X | X | X | X |
| Perfume oils 0.1-0.5% | X | X | X | X |
| UV-absorber composition comprising components (a), (b) and (c) according to the invention; 0.1-20% | X | X | X | X |
| UV-absorber as described in Table 2; 0-30% | X | X | X | X |

| Foaming/mousse products | |
|---|---|
| Ingredients | 1 |
| SD Alcohol 40 0-8% | X |
| Propellant 8-15% | X |
| Nonionic Emulsifier/Surfactant 0.5-3% | X |
| Corrosion Inhibitor 0-1% | X |
| Perfume oils 0.1-0.5% | X |
| Preservatives 0.1-1% | X |
| Miscellaneous 0-1% | X |
| UV-absorber composition comprising components (a), (b) and (c) according to the invention; 0.1-20% | X |
| UV-absorber as described in Table 2; 0-30% | X |

| Stick products | |
|---|---|
| Ingredients | 1 |
| Waxes 15-30% | X |
| Natural and silicone oils 20-75% | X |
| Lanoline derivatives 5->50% | X |
| Esters of lanolin | x |
| Acetylated lanolin | x |
| Lanolin oil | x |

-continued

Stick products

| Ingredients | 1 |
|---|---|
| Colorants and pigments 10-15% | X |
| Antioxidants 0.1-0.8% | X |
| Perfume oils 0.1-2% | X |
| Preservatives 0.1-0.7% | X |
| UV-absorber composition comprising components (a), (b) and (c) according to the invention; 0.1-20% | X |
| UV-absorber as described in Table 2; 0-30% | X |

Liquid and compact

| Ingredients | 1 | 2 |
|---|---|---|
| Liquid foundation | | |
| Powder phase 10-15% | X | |
| Oil phase 30%-40%; 75% (only for anhydrous form) | X | |
| Thickener/suspending agents 1-5% | X | |
| Film forming polymers 1-2% | X | |
| Antioxidants 0.1-1% | X | |
| Perfume oils 0.1-0.5% | X | |
| Preservatives 0.1-0.8% | X | |
| Water deionized Qs 100% | X | |
| Compact powder | | |
| Powder phase 15-50% | | X |
| Oil phase 15-50% | | X |
| Polyol phase 5-15% | | X |
| Antioxidants 0.1-1% | | X |
| Perfume oils 0.1-0.5% | | X |
| Preservatives 0.1-0.8% | | X |
| For the two product forms | | |
| UV-absorber composition comprising components (a), (b) and (c) according to the invention; 0.1-20% | X | X |
| UV-absorber as described in Table 2; 0-30% | X | X |

Conditioning Shampoos

| Ingredients | 1 |
|---|---|
| Primary surfactants (listed previously) 5-10% | X |
| Secondary surfactants (listed previously) 5-15% | X |
| Foam Stabilizers (listed previously) 0-5% | X |
| Water deionized 40-70% | X |
| Actives 0-10% | X |
| Conditioners | x |
| Refatting agents | x |
| Moisturizing agents | x |
| Thickeners/Rheology mofifiers 0-3% | X |
| Humectants 0-2% | X |
| PH adjusting agents 0-1% | X |
| Preservatives 0.05-1% | X |
| Perfume oils 0.1-1% | X |
| Antioxidants 0.05-0.20% | X |
| Chelating Agents (EDTA) 0-0.2% | X |
| Opascifying agents 0-2% | X |
| UV-absorber composition comprising components (a), (b) and (c) according to the invention; 0.1-20% | X |
| UV-absorber as described in Table 2; 0-30% | X |

The cosmetic preparation according to the invention is distinguished by excellent protection of human skin against the damaging effect of sunlight.

EXAMPLES

Preparation of the Samples for the Determination of the Photostability

2% of the compound of formula

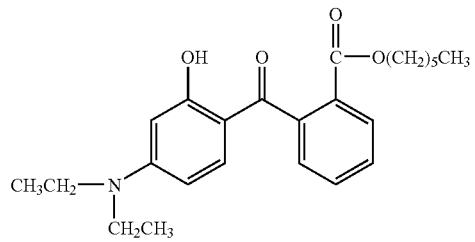
(101)

(Uvinul A Plus),

5% of the compound of formula

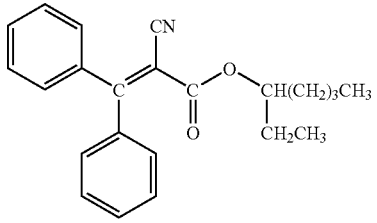
(102)

(Octocrylene) and

3% of the compound of formula

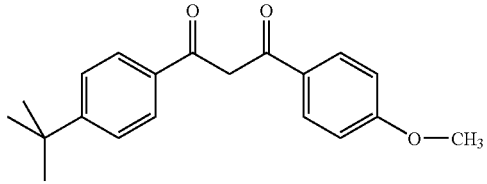
(103)

(Parsol 1789) are dissolved in a cosmetic carrier.

This composition (A) is applied on rough quartz-plates (2 µl/cm$^2$).

The times of irradiation are
0 h (no irradiation),
1 h (5 MED),
2 h (10 MED),
4 h (20 MED) and
10 h (50 MED)

with an Altas CPS+ sunlight simulator. For sufficient statistics 8 plates per time (x MED) are prepared. After irradiation, the samples can be recovered completely with a defined amount (5 ml) of a solvent (tetrahydrofurane).

HPLC:

The recovery of the UV-absorber was analyzed via HPLC:

| column: | Hypersil ODS 5 µm, 250 mm × 4 mm |
|---|---|
| Solvent A: | Water + 2 g/l TBAHS |
| Solvent B: | Acetonitrile/THF 9:1 + 2 g/l TBAHS |

-continued temperature: 35° C.
wavelength: 354 nm (for Detection of the compound of formula (101))

For comparison, the experiment is carried out in the same manner, but with a preparation comprising only
2% of the compound of formula (101) and
3% of the compound of formula (103) without the compound of formula (102) (=B).
The results: are listed in Table 2:

TABLE 3

Irradiation of UV absorber Compositions

| Irradiation | HPLC Recovery of the compound of formula (101) | |
| --- | --- | --- |
|  | Composition A | Composition B |
| No irradiation | 100% | 100% |
| 5 MED | 97% | 82% |
| 10 MED | 92% | 74% |
| 20 MED | 82% | 46% |
| 50 MED | 49% | 1% |

Composition A:
2% of the UV absorber of formula (101)
3% of the UV absorber of formula (103)
5% of the UV absorber of formula (102)
Composition B:
2% of the UV absorber of formula (101)
3% of the UV absorber of formula (103)
MED = Minimal Erythema Dose The results in Table 2 clearly demonstrate that the addition of the diphenylacrylate UV absorber of formula (102) (=Octocrylene) stabilizes the 2-hydroxybenzophenone UV absorber of formula (101) (=Uvinul A Plus) in a UV absorber composition which additionally comprises a UV absorber of formula (103 (=Parsol 1789; Avobenzone)

The invention claimed is:

1. A method for improving the UV stability of at least one component c) defined as an amino-substituted 2-hydroxybenzophenone derivative corresponding to formula

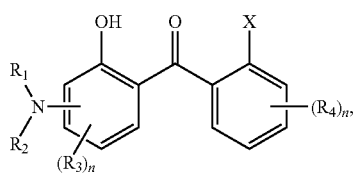

wherein
R$_1$ and R$_2$, independently from each other are hydrogen; C$_1$-C$_{30}$alkyl; C$_2$-C$_{10}$alkenyl; C$_3$-C$_{10}$ cycloalkyl; or C$_3$-C$_{10}$cycloalkenyl; or
R$_1$ and R$_2$ together form, with the nitrogen atom to which the are bonded a 5- or 6-membered heterocyclic ring member;
R$_3$ and R$_4$, independently from each other, are each C$_1$-C$_{20}$alkyl; C$_2$-C$_{10}$alkenyl; C$_3$-C$_{10}$cycloalkyl; C$_3$-C$_{10}$cycloalkenyl; C$_1$-C$_{12}$alkoxy; (C$_1$-C$_{20}$)alkoxycarbonyl; C$_1$-C$_{12}$alkylamino; di(C$_1$-C$_{12}$)alkylamino; an aryl or a heteroaryl radical which is optionally substituted; or a water-solubilizing substituent selected from a carboxylate group, a sulfonate group or an ammonium residue;

X is hydrogen; —COOR$_5$; or —CONR$_6$R$_7$;
R$_5$, R$_6$ and R$_7$, independently from each other, are hydrogen; C$_1$-C$_{20}$alkyl; C$_2$-C$_{10}$alkenyl; C$_3$-C$_{10}$cycloalkyl; C$_3$-C$_{10}$cycloalkenyl, —(Y'O)$_o$—Z'; or aryl;
Y' is —(CH$_2$)$_2$—; —(CH$_2$)$_3$—; —(CH$_2$)$_4$—; or —CH—(CH$_3$)—CH$_2$—;
Z' is —CH$_2$—CH$_3$; —CH$_2$—CH$_2$CH$_3$; —CH$_2$CH$_2$—CH$_2$—CH$_3$ or —CH(CH$_3$)—CH$_3$;
n is an integer from 0 to 3; and
o is an integer from 1 to 2,
in the presence of (b) at least one dibenzoylmethane derivative;
which method comprises adding to a
cosmetic or dermatological composition comprising c) and b) an effective photo-stabilizing amount of a UV filter
(a) defined by formula (I)
2-ethylhexyl2-cyano,3,3-diphenylacrylate of formula.

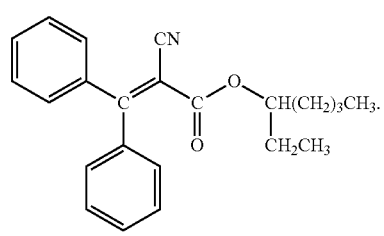

2. A method according to claim 1, wherein the stabilizing agent (a) is used in a concentration from 1 to 10 weight % based on total weight of the cosmetic or dermatological composition.

3. A method according to claim 1, wherein the dibenzoylmethane derivative (b) is 4-tert-butyl-4'-methoxydibenzoylmethane.

4. A method according to claim 1, wherein the 2-hydroxybenzophenone derivative (c) corresponds to formula

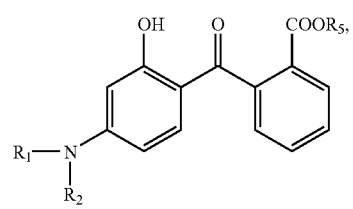

wherein
R$_1$ and R$_2$, independently from each other, are hydrogen; or C$_1$-C$_8$alkyl; or together form, with the nitrogen atom to which they are bonded, a 5- or 6-membered heterocyclic ring member; and
R$_5$ is hydrogen; C$_1$-C$_5$alkyl; or a C$_3$-C$_6$cycloalkyl.

5. A method according to claim 1, wherein the 2-hydroxybenzo-phenone derivative (c) corresponds to formula

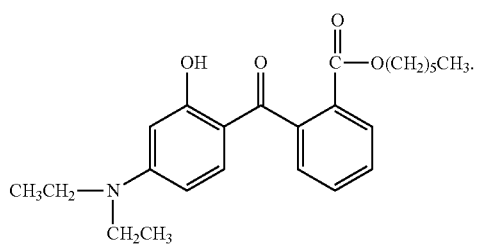

(7)

6. A method according to claim 1, wherein the cosmetic or dermatological composition comprises at least
   1.0 to 10 weight % of a stabilizing agent (a) as defined in claim 1 based on total weight of said composition,
   2.0 to 5 weight % of a dibenzoylmethane derivative (b) based on total weight of said composition; and
   0.3 to 10 weight % of an amino-substituted 2-hydroxybenzophenone derivative (c) based on total weight of said composition.

7. A cosmetic or dermatological composition comprising at least
   1.0 to 10 weight % of a stabilizing agent (a) as defined in claim 1 based on total weight of said composition;
   2.0 to 5 weight % of a dibenzoylmethane derivative UV filter (b) based on total weight of said composition; and
   0.3 to 10 weight % of an amino-substituted 2-hydroxybenzophenone derivative UV filter (c) based on total weight of said composition.

8. The method according to claim 1, wherein the 2-hydroxybenzo-phenone derivative (c) corresponds to formula

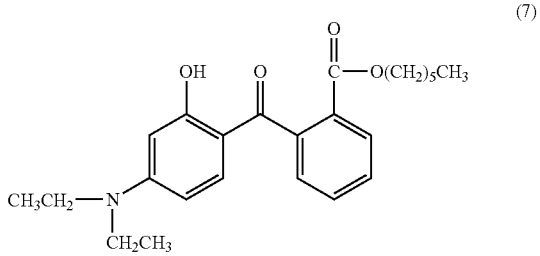

(7)

and the dibenzoylmethane derivative (b) is 4-tert-butyl-4'-methoxydibenzoylmethane.

* * * * *